United States Patent [19]

Stephens

[11] 4,421,296
[45] Dec. 20, 1983

[54] DISPOSABLE PLASTIC RECIPROCATING VALVE

[75] Inventor: James W. Stephens, Memphis, Tenn.

[73] Assignee: Medical Valve Corporation, Memphis, Tenn.

[21] Appl. No.: 291,948

[22] Filed: Aug. 11, 1981

Related U.S. Application Data

[63] Continuation-in-part of Ser. No. 169,642, Jul. 17, 1980, abandoned.

[51] Int. Cl.³ .............................................. F16L 37/28
[52] U.S. Cl. .............................. 251/149.7; 251/149.6; 604/99; 604/256
[58] Field of Search .................. 604/99, 256, 33, 249; 251/149.6, 149.7

[56] References Cited

U.S. PATENT DOCUMENTS

| 3,087,492 | 4/1963 | Garth | 604/99 |
| 3,385,301 | 5/1968 | Harautuneian | 604/99 |
| 3,806,086 | 4/1974 | Cloyd | 251/149.7 |

Primary Examiner—A. Michael Chambers
Attorney, Agent, or Firm—Littlepage & Webner

[57] ABSTRACT

A disposable normally closed all plastic reciprocating valve is adapted to be used in a supply line for fluids supplied to or extracted from a patient. The valve is opened by inserting a tube into one end thereof.

4 Claims, 8 Drawing Figures

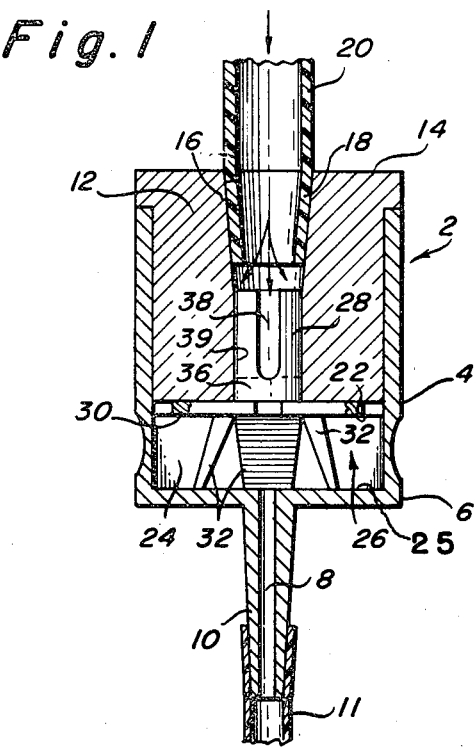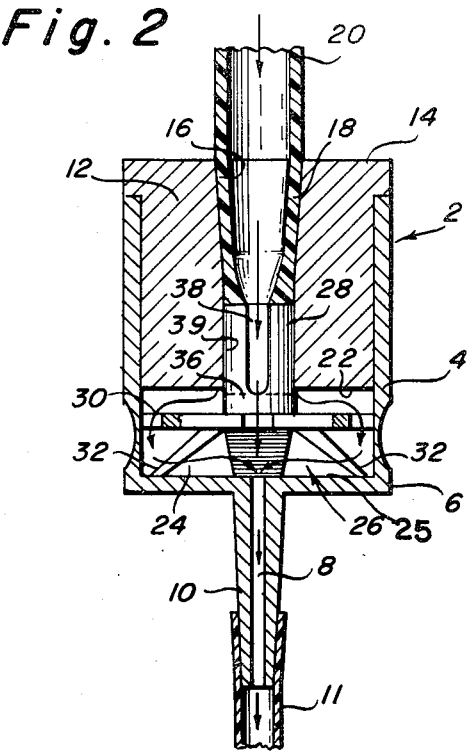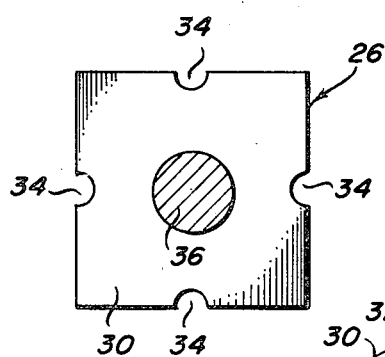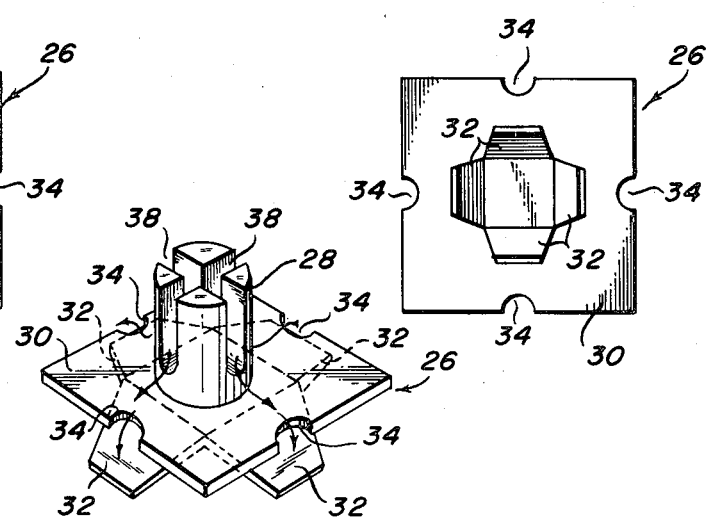

DISPOSABLE PLASTIC RECIPROCATING VALVE

RELATED APPLICATION

Stephens PLASTIC RECIPROCATING VALVE, Ser. No. 169,642 filed July 17, 1980, now abandoned, of which this is a continuation-in-part.

FIELD OF INVENTION

Valves and Valve Actuation, Reciprocating Valve, Push or Pull Operator, Spring

PRIOR ART

Vidy U.S. Pat. No. 1,066; and Muffler U.S. Pat. No. 3,355,143

OBJECTS

The primary object of this invention is to provide a normally closed valve for use between two tubes in a fluid line, and which valve is opened by insertion of one of the tubes into one end of the valve casing. The principal feature of the valve is that it is formed of only three easily moldable plastic parts which are simply fitted together, the valve being completely sanitary or sanitizable and so inexpensive to manufacture that it is disposable without much loss.

These and other objects will be apparent in the following specification and drawing, in which:

FIG. 1 is a longitudinal cross section through the valve showing the valve closed;

FIG. 2 is a view similar to FIG. 1 but showing the valve open;

FIG. 3 is a top plan view of the valve disc showing the bottom of the stem in cross-section;

FIG. 4 is a bottom plan view of the valve disc;

FIG. 5 is a perspective view of the valve.

Figure 6:
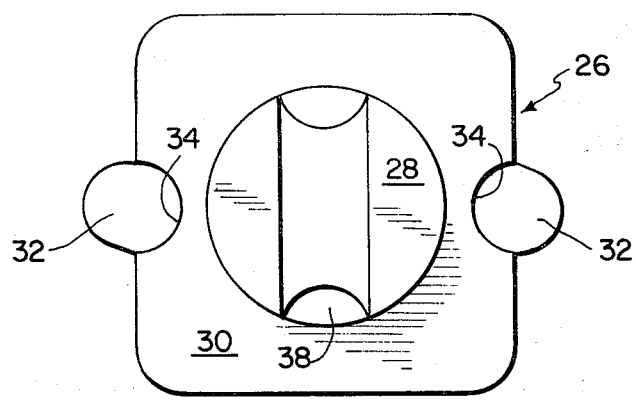
FIG. 6 is a top plan view showing a modified form of the spring legs which normally hold the valve closed until a tube is inserted into the input end of the valve.

Referring now to the drawing, the valve 2 has a casing comprised of a generally cylindrical outer shell 6 having a service port 8 at one end registering with a nipple 10 over which one of tubes 11 of a fluid supply line is engaged. Into the end of shell 6 opposite service port 8, which end is open, is a plug 12, which can be friction-fit into the shell 6 if the valve is to be taken apart for cleaning, or which can be cemented into the shell if the valve is to be disposed of after usage. Plug 12 has a cap flange 14 which fits against the end of shell 6 and a bore 16 for receiving a syringe 18 on the end of the other tube 20 of the fluid line. The bottom side 22 of plug 12 constitutes a valve seat which is spaced above the lower end of shell 6 so as to define therebetween a valve chamber 24 in which the reciprocating valve 26 is disposed.

Reciprocating valve 26 has a stem 28 which has a free end against which the syringe 18 engages. On the lower end of valve stem 28 is a disc 30 which normally engages against the seat 22 on the underside of plug 12. Depending from valve disc 30 are springy legs 32 which engage against the end wall 25 of valve chamber 24 and normally press the valve disc 30 against the seat 22. In the periphery of valve disc 30 are cut-out ports 34. The lower end of valve stem 28 is closed, as indicated at 36 and through the sides of valve stem 28 are slotted ports 38 which are normally masked by the wall 39 of the plug bore 16.

In operation, the springy legs 32 which depend from valve disc 30 normally press the latter against the bottom seat 22 on the underside of plug 12 and, in this condition, the ports 38 in the valve stem are masked by the wall 39 of plug bore 16. However, when the syringe 18 is inserted into the hollow valve stem 28 and pushed in, the valve disc 30 is thereby forced against the bias of the spring legs 32 away from the seat 22 and likewise the ports 38 in valve stem 28 are unmasked below the lower end of the inner wall surface 39 of plug bore 16 so that fluid-flow communication is established from chamber 24 via the cut-out ports 34, the space between the seat 22 and the disc 30, and through ports 38 and thence to the lower end of the syringe 18.

Figure 7:
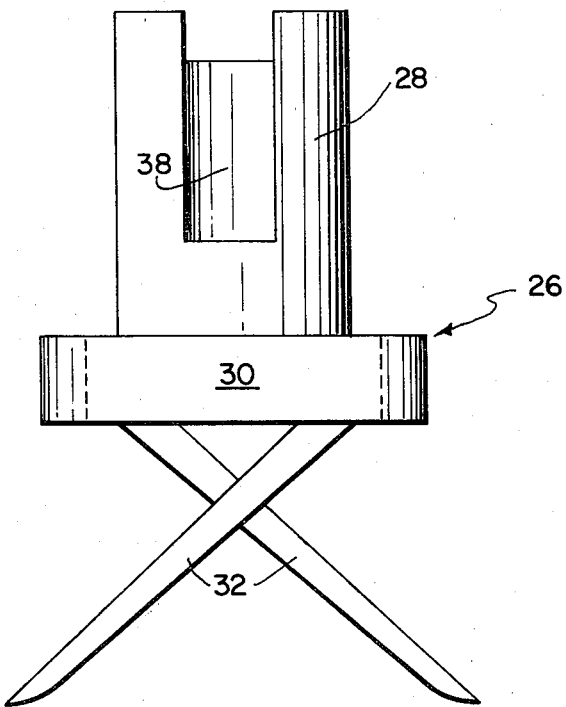
FIG. 7 is a side elevation of the modification shown in FIG. 6.
Figure 8:
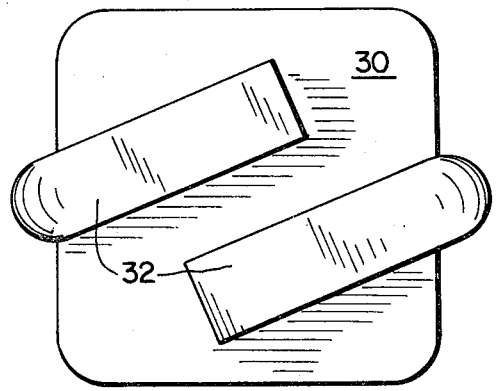
FIG. 8 is a bottom view of this modification shown in FIGS. 6 and 7.

The modification shown in FIGS. 6, 7 and 8 is identical to the valve illustrated in FIGS. 1–5 except for the form of the springy legs 32a. These legs are crossed so as to provide maximum spring lengths, and their lower free ends do not slide against the inner surface of the lower end wall 25 of the valve casing as do the legs 32.

I claim:

1. A reciprocating valve comprising, a generally cylindrical hollow casing enclosing a valve chamber defined between axially-spaced inner walls of said casing, one of which walls constitutes a valve seat, said casing having a bore extending axially therein from one end thereof and through said seat into said chamber, a reciprocating valve comprising a disc disposed in said chamber, said disc having port means therethrough, stem means on one side thereof reciprocable in said bore, and spring leg means on the other side thereof for engaging the other inner wall of said chamber so as normally to force said disc in seating engagement against said seat, service port means for said chamber, said stem means having an open hollow free end portion constituting a service port for receiving a fluid coupling member, a closed end portion integral with said disc, and port means extending from the hollow free end portion to the periphery of the stem, said port means through the stem and disc being normally masked by the wall of said bore and said seat, respectively, when said spring legs force the valve in one direction to engage the disc against said seat, and being open when said fitting engages into said stem socket and forces the valve member in the other direction against the forces of said spring legs so as to space the disc from the seat and thereby unmask the port means therethrough while moving the port means in the stem beyond the wall of the bore and thereby unmask the same whereby to establish a fluid path from the socket, the port means in the stem, the space between the disc and the seat, the port means in the disc, the valve chamber, and the service port means for the chamber.

2. A reciprocating valve as claimed in claim 1, said reciprocating valve being a one piece plastic member of which the disc, stem means and spring leg means are integral parts.

3. A reciprocating valve as claimed in claim 2, the port means through the disc comprising cut-outs in the periphery thereof.

4. A reciprocating valve as claimed in claim 3, there being a plurality of the port means through the disc which are spaced about the periphery thereof and there being a plurality of spring leg means which are intersperced between the disc port means.

* * * * *